US012653960B2

(12) United States Patent
Fischer et al.

(10) Patent No.: US 12,653,960 B2
(45) Date of Patent: Jun. 16, 2026

(54) SAFETY COVER FOR COUPLING WITH AN INJECTION DEVICE

(71) Applicants: Stephan Fischer, Hiddenhausen (DE); Tobias Wilke, Ibbenbueren (DE); Bernd Mohr, Barnstedt (DE)

(72) Inventors: Stephan Fischer, Hiddenhausen (DE); Tobias Wilke, Ibbenbueren (DE); Bernd Mohr, Barnstedt (DE)

( * ) Notice: Subject to any disclaimer, the term of this patent is extended or adjusted under 35 U.S.C. 154(b) by 736 days.

(21) Appl. No.: 18/126,878

(22) Filed: Mar. 27, 2023

(65) Prior Publication Data

US 2023/0398312 A1      Dec. 14, 2023

Related U.S. Application Data

(63) Continuation of application No. PCT/EP2021/075159, filed on Sep. 14, 2021.

(30) Foreign Application Priority Data

Oct. 7, 2020 (DE) ............................ 102020126258

(51) Int. Cl.
*A61M 5/32* (2006.01)

(52) U.S. Cl.
CPC ... *A61M 5/3216* (2013.01); *A61M 2005/3217* (2013.01)

(58) Field of Classification Search
CPC ........ A61M 5/3216; A61M 2005/3217; A61M 5/3202; A61M 5/00
See application file for complete search history.

(56) References Cited

U.S. PATENT DOCUMENTS

| | | | | |
|---|---|---|---|---|
| 5,599,313 | A | 2/1997 | Gyure | |
| 5,632,732 | A * | 5/1997 | Szabo | ................. A61M 5/3216 604/263 |
| 12,064,609 | B2 * | 8/2024 | Madin | ................. A61M 5/3216 |
| 2011/0301546 | A1 | 12/2011 | Harms | |
| 2020/0246553 | A1 | 8/2020 | Wilke | |

* cited by examiner

*Primary Examiner* — Bhisma Mehta
*Assistant Examiner* — Fatimata Sahra Diop
(74) *Attorney, Agent, or Firm* — Von Rohrscheidt Patents

(57) ABSTRACT

A safety cover for coupling with an injection device, the safety cover including a base; a cover including an outer housing and an inner housing; and a hinge, wherein the base includes a needle mount which is configured for directed receiving of an injection needle along a receiving axis of the needle mount, wherein the outer housing is coupled with the inner housing in a coaxial arrangement relative to a longitudinal axis of the cover and mounted at the inner housing, at least partially surrounding the inner housing, wherein the cover is connected by the hinge with the base, so that the cover is pivotable relative to the base about a pivot axis formed by the hinge and oriented perpendicular to the receiving axis so that that the cover is pivotable from an initial position in a first pivoting direction into a treatment position.

14 Claims, 10 Drawing Sheets

SAFETY COVER FOR COUPLING WITH AN INJECTION DEVICE

RELATED APPLICATIONS

This application is a continuation of International patent application PCT/EP2021/075159 filed on Sep. 14, 2021 claiming priority from German patent application 10 2020 126 258.2 filed on October, 2020, both of which are incorporated in their entirety by this reference.

FIELD OF THE INVENTION

The present application relates to a safety cover for coupling with an injection device.

BACKGROUND OF THE INVENTION

Safety covers of the type described in the introduction are already known in the prior art. For this, reference is to be made in particular to the international patent application WO 2018/172853 A1. This describes a generic safety cover, which creates a secure housing of the injection needle before and after an injection. The use of the safety cover in connection with the associated injection device takes place here in a particular sequence:

On putting into use the injection device, which cooperates with the safety cover, the cover is firstly present in its initial position. In this initial position, long recesses of the inner housing and of the outer housing of the cover, extending parallel to a longitudinal axis of the cover, are arranged overlapping one another. The cover is connected as a whole with a base by means of a hinge element, so that the cover is pivotable relative to the base about a pivot axis of the hinge element. This pivotability is utilized in order to transfer the cover into its treatment position. In the course of the pivoting, the injection needle penetrates through the recesses of the outer housing and of the inner housing which are overlapping one another, and is then exposed. The injection device is now able to be used, in order to inject a patient with a respective medicament. After use, the cover can be pivoted back into its initial position again by means of the hinge element, so that the injection needle is spatially enclosed again by the cover. In this state, it is basically possible to free the injection needle by means of a repeated transfer of the cover into the treatment position. This is not desired, because basically a risk of injury and hence a risk of injection proceed from the injection needle. In order to therefore prevent the repeated freeing of the injection needle, the outer housing can be twisted by means of a grip element relative to the inner housing through 180° about the longitudinal axis of the cover, so that the elongated recesses of the inner housing and of the outer housing no longer overlap one another. The outer housing is locked here on the inner housing, so that the outer housing is present in a locking position. Following therefrom, it is no longer possible to free the injection needle by means of pivoting the cover. Owing to the locking of the outer housing on the inner housing, furthermore the original initial position of the outer housing, at the presence of which the recesses of the outer housing and of the inner housing have overlapped one another, is no longer able to be produced.

The known safety cover can be disadvantageous in connection with particular injection devices which require a screwing of the safety cover together with an injection needle, thus typically necessary in syringes with a so-called luer lock connection. In most injection devices, it is usual that the safety cover together with the injection needle is merely placed on at a front end of the injection device, thus for example in syringes with a so-called luer slip connection. In such injection devices, the known safety cover is readily able to be used. In injection devices with a "screw connection", however, it can be problematic that the outer housing and the inner housing are able to be twisted relative to one another. Thus, it has been found in application that the safety cover, fastened by screw connection on the injection device, together with the injection needle, for the sake of safety is "re-tightened" once again manually by a user of the injection device, i.e. for the purpose of secure screwing, a torque is exerted onto the safety cover. This re-tightening requires a rotation of the safety cover in clockwise direction. In so far as the user grips the outer housing during this movement, a transferring of the outer housing into its locking position can occur unintentionally, in which the outer housing from this time on is locked relative to the inner housing. The injection needle would thereupon be enclosed in the cover irretrievably, so that the cover—as is otherwise also desired as a result of the transfer of the outer housing into its locking position—can no longer be transferred into its treatment position.

BRIEF SUMMARY OF THE INVENTION

The present application is therefore based on the problem of providing a safety cover which is protected from a maloperation in the context of an injection device with a screw connection.

The underlying problem is solved according to the invention by a safety cover, which is provided for single use, comprises a base, a cover and a hinge element, wherein the base is connected with the cover by means of the hinge element. The base comprises a needle mount which is suitable to receive an injection needle. Here, the needle mount is configured in such a manner that a received injection needle, which is straight per se, extends along a receiving axis. The base preferably has a rotationally symmetrical shape.

The cover comprises an outer housing and an inner housing arranged coaxially to the outer housing. The outer housing and the inner housing are coupled with one another, wherein the outer housing is mounted on the inner housing and surrounds the latter at least partially. The hinge element is connected, on the one hand, with the base, and on the other hand with the inner housing, wherein via the connection with the inner housing, the connection with the cover as a whole is produced.

The hinge element, which is preferably associated both with the base and also with the cover respectively on the edge side, forms a pivot axis which is oriented perpendicularly to the receiving axis of the needle mount. The hinge element can be formed in particular by a film hinge. By means of the hinge element, the cover can be pivoted relative to the base about the pivot axis, wherein the cover, proceeding from an initial position, is pivotable in a first pivoting direction into a treatment position. On presence in the initial position, a longitudinal axis of the cover is aligned parallel to the receiving axis of the needle mount. The needle mount is preferably formed at an upper end of the base and is preferably centred on the base, so that the cover, which likewise adjoins thereto at the upper end of the base, on presence in its initial position, surrounds the needle mount radially. This has the result that an injection needle received in the needle mount is enclosed or respectively surrounded spatially by the cover, in so far as the cover is present in its initial position. By comparison, the cover, on presence in its treatment position, is pivoted with respect to the base around the pivot axis, so that the longitudinal axis of the cover is pivoted with respect to the receiving axis of the needle mount. In other words, the cover, on presence in its treatment position, is "laterally pivoted away" with respect to the initial position, so that the injection needle situated in the needle mount is freed for use. In the course of the pivoting of the cover, the injection needle is consequently freed.

The outer housing is able to be twisted relative to the inner housing at least in one rotation direction around the longitudinal axis of the cover. For this purpose, the outer housing and the inner housing have respectively preferably a rotationally symmetrical shape. The outer housing has at least one recess, which is suitable to cooperate with at least one locking device arranged on the base. Said locking device—in relation to the receiving axis of the needle mount—projects radially outwards and is configured so that it can engage with the recess of the outer housing in a form-fitting manner, in so far as the outer housing is present in a locking position which is twisted with respect to the inner housing. This locking has the result that a further twisting of the outer housing relative to the inner housing is blocked. The form fit acts therefore at least in circumferential direction of the cover.

The safety cover according to the invention is characterized in that the base comprises at least one locking device, by means of which the base engages with the outer housing in a form-fitting manner, so that a twisting of the outer housing relative to the inner housing is blocked. This engagement of the locking device with the outer housing is present at least on the presence of the outer housing in its initial position and on the presence of the cover in its initial position. The starting position of the outer housing differs from its locking position, wherein the outer housing has its starting position at least on the presence of the cover in its initial position. In so far as the outer housing and the inner housing—as described above with regard to the prior art—have elongated recesses overlapping one another, the position of the outer housing is to be understood as starting position in which the recesses of the inner housing and of the outer housing overlap one another. The locking position in such an embodiment, on the other hand, is achieved when the recesses no longer overlap one another, wherein the outer housing for example can be twisted through 180° about the longitudinal axis of the cover relative to the inner housing.

The safety cover according to the invention is furthermore characterized in that the outer housing is displaceable with respect to the base and in this way the cover is able to be transferred into an end position. On presence in this end position, the engagement of the locking device with the outer housing is terminated, so that the twisting of the outer housing relative to the inner housing is freed. The outer housing, on presence of the cover in its end position, can therefore be transferred into its locking position.

The safety cover according to the invention has several advantages. In particular, it permits the ability of the outer housing to be twisted relative to the inner housing, known from the prior art, to be basically maintained, in order to finally transfer the outer housing into its locking position and to bring about the desired secure surrounding of the respective injection needle by means of the cover. The form-fitting connection according to the invention of at least one locking device with the outer housing on presence of the latter in its initial position has, in addition, the technical effect that the outer housing nevertheless can not be twisted with respect to the inner housing when the cover is still situated in its initial position. In this initial position of the cover, the ability to be twisted is (still) not desired. On the contrary, the outer housing and the inner housing are effectively locked with respect to one another by means of the locking device, so that—as described above—a user of the injection device can "re-tighten" the safety cover once again before use of the injection device, i.e. can apply a torque onto the outer housing without, in so doing, inadvertently already twisting the outer housing prematurely relative to the inner housing and thereby transferring it into its locking position.

As nevertheless the twisting ability of the outer housing and inner housing is to be made possible, in order to finally securely enclose the injection needle after the injection has been completed, provision is made according to the invention to carry out the twisting of the outer housing relative to the inner housing not proceeding from the initial position of the cover, but rather proceeding from the end position. This is achieved when at least the outer housing, preferably the entire cover, is displaced relative to the base with respect to the initial position. The end position is, in addition, characterized in that on its presence the form-fitting engagement of the locking device with the outer housing is terminated, so that basically in a comparable manner to the prior art the outer housing is able to be twisted with respect to the inner housing, in this way is able to be transferred into its locking position and hence the injection needle is able to be enclosed securely.

In the use of the safety cover according to the invention, consequently after an injection has been completed, an additional step is necessary compared to the prior art, namely the transferring of the cover into its end position. In detail therefore the safety cover as a whole can be operated as follows: At the start of a respective injection, the cover is firstly present in its initial position. In this initial position, typically the longitudinal axis of the cover and the receiving axis of the needle mount are arranged parallel to one another, preferably congruently. The safety cover is screwed onto an injection device, which in particular can be equipped with a screw connection, for example in the form of a luer lock connection. On presence in the initial position, the outer housing according to the invention as a result of the engagement of a locking device with the outer housing is secured against an (unintentional) twisting of the outer housing relative to the inner housing. Any re-tightening or respectively tight screwing of the safety cover for a better fastening thereof on the injection device which is desired by the user of the injection device can therefore take place readily by means of applying a torque onto the outer housing. The locking of the outer housing with the base has the result here that the applied torque is transferred from the outer housing to the base and finally the desired re-tightening of the safety cove can be achieved. Proceeding from the initial position, the cover is transferred into its treatment position, on the presence of which the respective injection needle is freed. This procedure is analogous to the prior art and is already described above. After the injection has been completed, the cover is transferred back into its initial position, in which the injection needle is spatially enclosed by the cover. Having arrived in this initial position, in the safety cover according to the invention, the twisting of the outer housing relative to be inner housing, which is desired in the prior art, is still blocked. Therefore, provision is now made to transfer the cover, proceeding from the initial position further into its end position, in which the form fit between the locking device and the outer housing is terminated. After this termination, the outer housing is able to be twisted relative to the inner housing in a comparable manner to the prior art. The former is hereby transferred into its locking position in a comparable manner to the prior art, in which the injection needle is securely enclosed by means of the cover. The operation of the injection device together with the safety cover according to the invention is thus completed. The safety cover can therefore now be removed from the injection device, in particular screwed off, and disposed of.

In a particularly advantageous embodiment of the safety cover according to the invention, the basis comprises a locking device which is configured both for the form-fitting engagement with the recess of the outer housing on presence thereof in its locking position, and also for the form-fitting engagement with the outer housing on presence thereof in its initial position. In other words, the locking device in this embodiment has a dual function, namely the securing of the locking of the outer housing with respect to the inner housing on presence of the outer housing both in its initial position and also in its locking position. In a particularly advantageous manner, the locking device can be configured in the form of a radially outwardly projecting pin. Such a pin can extend in particular further outwards radially with respect to the receiving axis of the needle mount than an outer covering surface of the outer housing in the region of the pin. In such a configuration, the pin projects to some extent into the covering surface or respectively into a recess of the outer housing situated there, and therefore prevents a rotation of the outer housing relative to the base about the longitudinal axis of the cover.

The described embodiment of the safety cover with a locking device configured as a radially extending pin is then particularly to be preferred when the locking device is arranged lying diametrically opposite the hinge element on the basis. Here, the hinge element is preferably arranged on the edge side on the base or respectively adjoining an outer edge of the base. This has the characteristic that in such an arrangement, the cover is pivotable by means of the hinge element about the associated pivot axis in such a way that by means of the pivoting a displacement of the outer housing can take place in the direction of a longitudinal axis of the pin-shaped, radially extending locking device. For this, it is furthermore particularly advantageous if the locking device and the pivot axis of the hinge element are spaced apart from one another measured in a direction parallel to the receiving axis of the needle mount. This configuration has the result that a pivoting of the cover about the pivot axis, owing to the described distance, results in a movement with a lateral or respectively radial, in relation to the receiving axis of the needle mount, movement component of the cover and therefore of the outer housing. This movement is suitable in order to move the outer housing in radial direction relative to the radially extending locking device just so far that the engagement of the locking device with the outer housing is terminated. In particular, the outer housing can be moved in radial direction relative to the receiving axis beyond a distal end of the locking device, so that the outer housing to some extent surrounds the locking device entirely. The engagement of the locking device with the recess of the outer housing is then no longer present, so that the outer housing from now on is able to be twisted relative to the base and to the inner housing and finally is able to be transferred into its locking position as desired.

Furthermore, it can be particularly advantageous if the cover is pivotable by means of the hinge element into a second pivoting direction, opposed to the first pivoting direction, proceeding from its initial position about the pivot axis into the end position, whereby the displacement of the outer housing with respect to the base and therefore with respect to the locking device is able to be achieved. This displacement is then accompanied, as described, by the termination of the form fit between the locking device and the outer housing. On presence in the end position, the cover is preferably pivoted so far with respect to the initial position that the longitudinal axis and the receiving axis of the needle mount form an angle of at least 5°, preferably at least 7°.

In a particularly advantageous embodiment, the outer housing comprises at least a second recess, which is arranged for the form-fitting engagement with the locking device of the base. Advantageously, the two recesses of the outer housing are arranged offset by 180° in relation to the longitudinal axis of the cover. The embodiment of the outer housing with two recesses enables the locking of the outer housing relative to the base or respectively to the inner housing in different positions, namely in particular the initial position and the locking position The recess which produces the form fit with a locking device on presence of the outer housing in its initial position can be configured in a particularly advantageous manner to be elongated in axial direction of the outer housing and extend, proceeding from a proximal end of the cover, in the direction of a distal end of the cover. Advantageously, this elongated recess has a length of at least 2.0 cm, preferably at least 3.0 cm, measured parallel to the longitudinal axis of the cover. Such a cover is particularly well suited to free the respective injection needle, held in the needle mount, in the course of the transfer of the cover proceeding from its initial position into its treatment position. The injection needle can thus exit from the cover through the recess in the course of the transfer of the cover in its treatment position, so that it is from then on exposed for the treatment of the respective patient. Vice versa, after completion of the treatment, the injection needle can enter into the cover again through the recess on transferring of the cover back in the direction of its initial position, so that it is situated again spatially inside the cover.

Similarly, it can be particularly advantageous if the inner housing has at least one recess which extends along the longitudinal axis of the cover, wherein the recess proceeds from a proximal end of the cover and extends in the direction of a distal end of the cover. Similarly to an advantageous embodiment of a recess of the outer housing, it is also advantageous for the recess of the inner housing if this has a length of at least 2.0 cm, preferably at least 3.0 cm, measured parallel to the longitudinal axis of the cover.

Advantageously, the inner housing and the outer housing have recesses corresponding with one another, preferably respectively in the elongated form described above, which on presence of the cover in its initial position overlap one another and thus enable an exit of an injection needle out of the cover and a subsequent re-entry of the injection needle into the cover. The recesses of the outer housing and of the inner housing correspond here advantageously to one another in their shape and in their length measured parallel to the longitudinal axis of the cover.

Advantageously, the recesses of the outer housing and of the inner housing, on presence of the outer housing in its locking position, are offset with respect to one another, so that the passage of the injection needle, described above, jointly through both recesses is no longer possible. Hereby it is prevented that the cover is transferred into its treatment position, in which the injection needle is freed. Consequently, an injury with the injection needle is prevented.

Furthermore, such an embodiment of the safety cover according to the invention can be advantageous which comprises an interlocking mechanism which has respectively an interlocking partner on the base and on the cover. The interlocking partner, arranged on the cover, is advantageously arranged on the inner housing of the cover. The interlocking partners of base and cover are arranged to engage with one another in a detaining manner when the cover is present in its end position. In this way, it is possible to fix the cover in its end position. This embodiment has the advantage that the safety cover, after being used once, has been visibly externally already used, because the cover is situated in its end position and remains therein. An inadvertent perception of the respective safety cover as being still unused is thus ruled out as far as possible.

Finally, such an embodiment of the safety cover can be advantageous, the base of which has a radially projecting, circumferential collar, by means of which the base can cooperate with a thread of an injection device. In particular, the collar can project radially outwards, as it is usual that the injection device EN is equipped with a thread configured as an internal thread. By means of the collar, it is consequently made possible to screw the safety cover onto a correspondingly configured injection device.

BRIEF DESCRIPTION OF THE DRAWINGS

The invention is explained more closely below with the aid of an example embodiment, which is illustrated in the figures. There are shown.

DETAILED DESCRIPTION OF THE INVENTION

Figure 1:
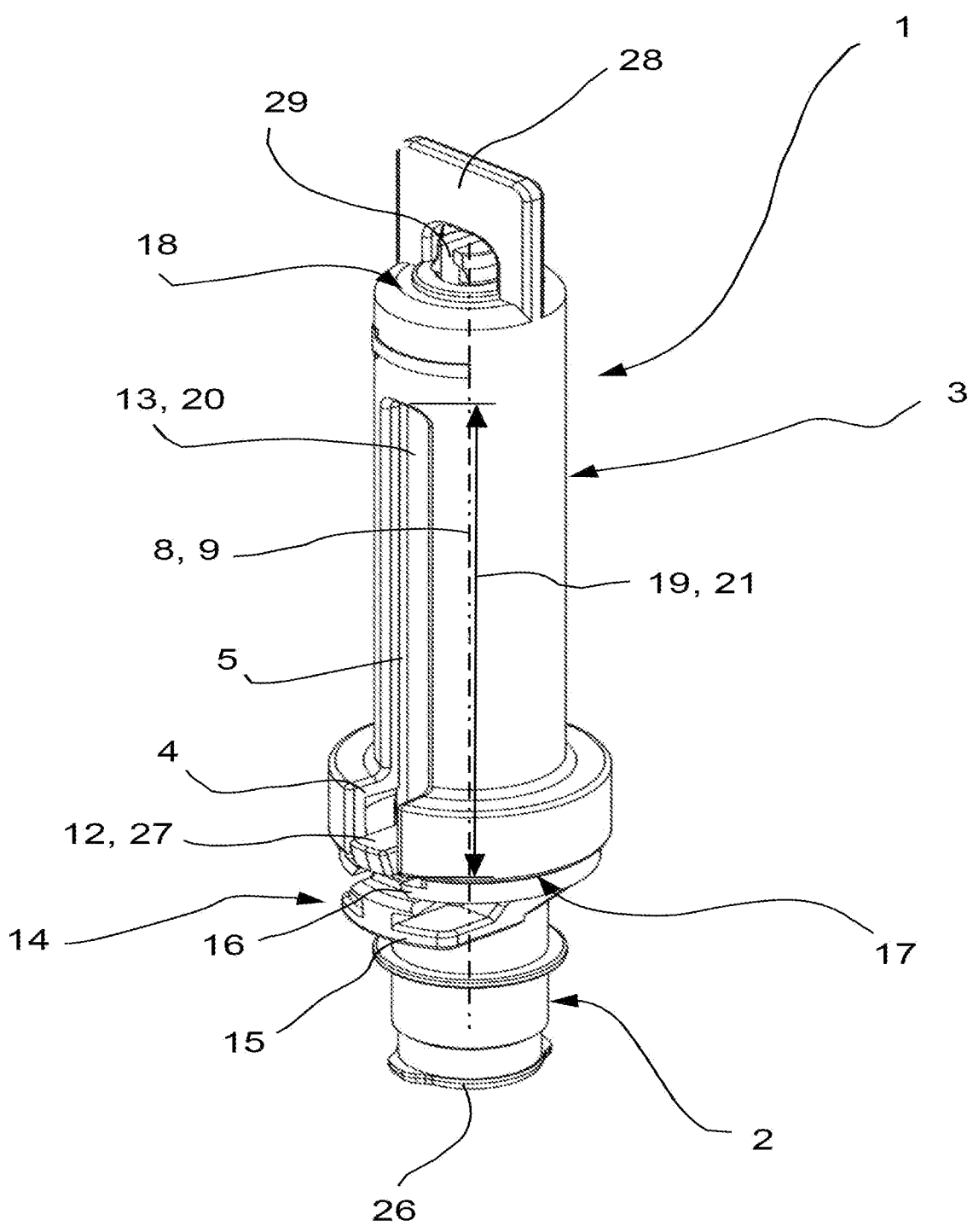
FIG. 1: A view of a safety cover according to the invention on presence of a cover of the safety cover in its initial position.
Figure 2:
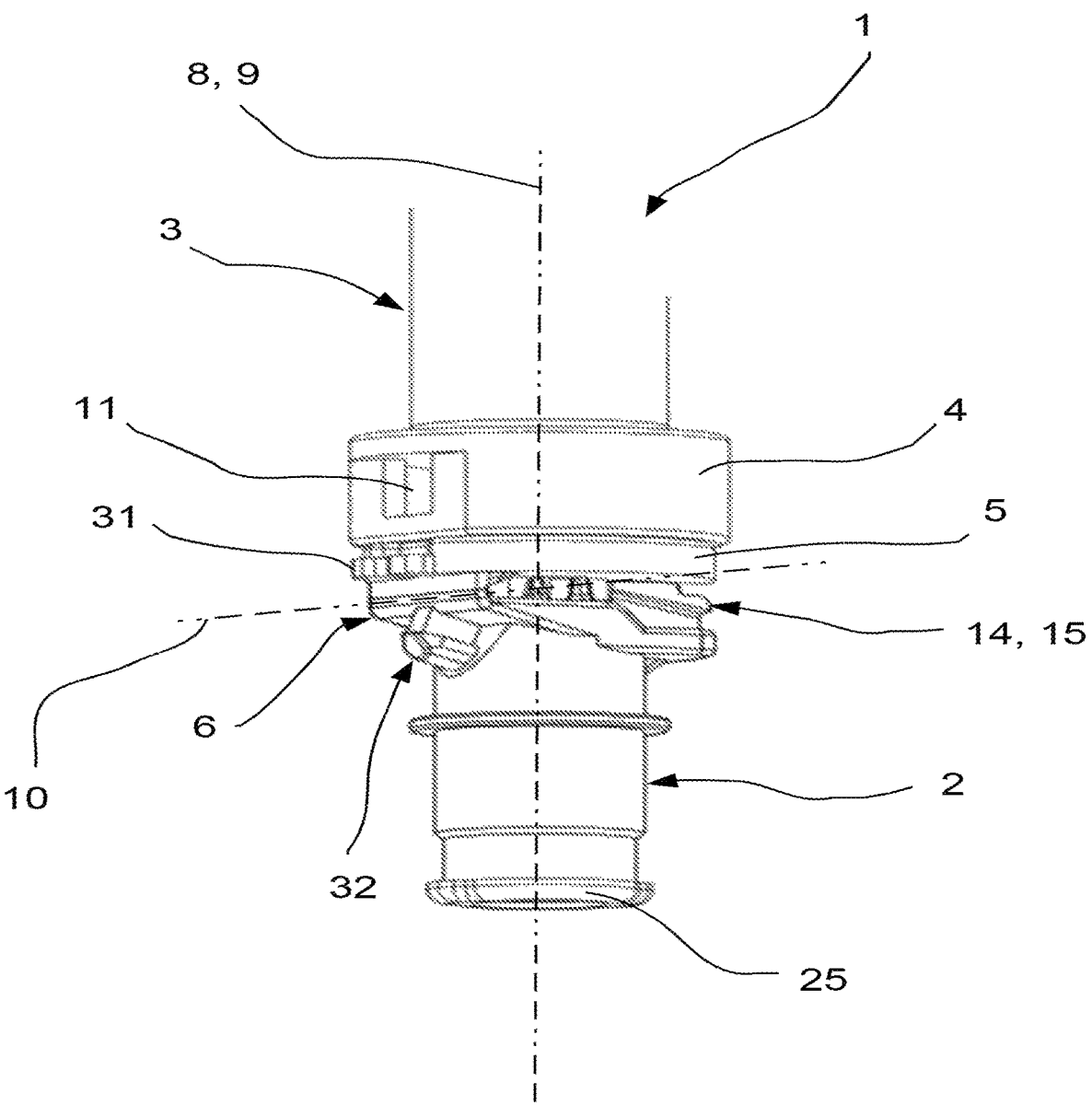
FIG. 2: The safety cover according to FIG. 1, however in the region of a base of the safety cover, viewed from a rear side.
Figure 3:
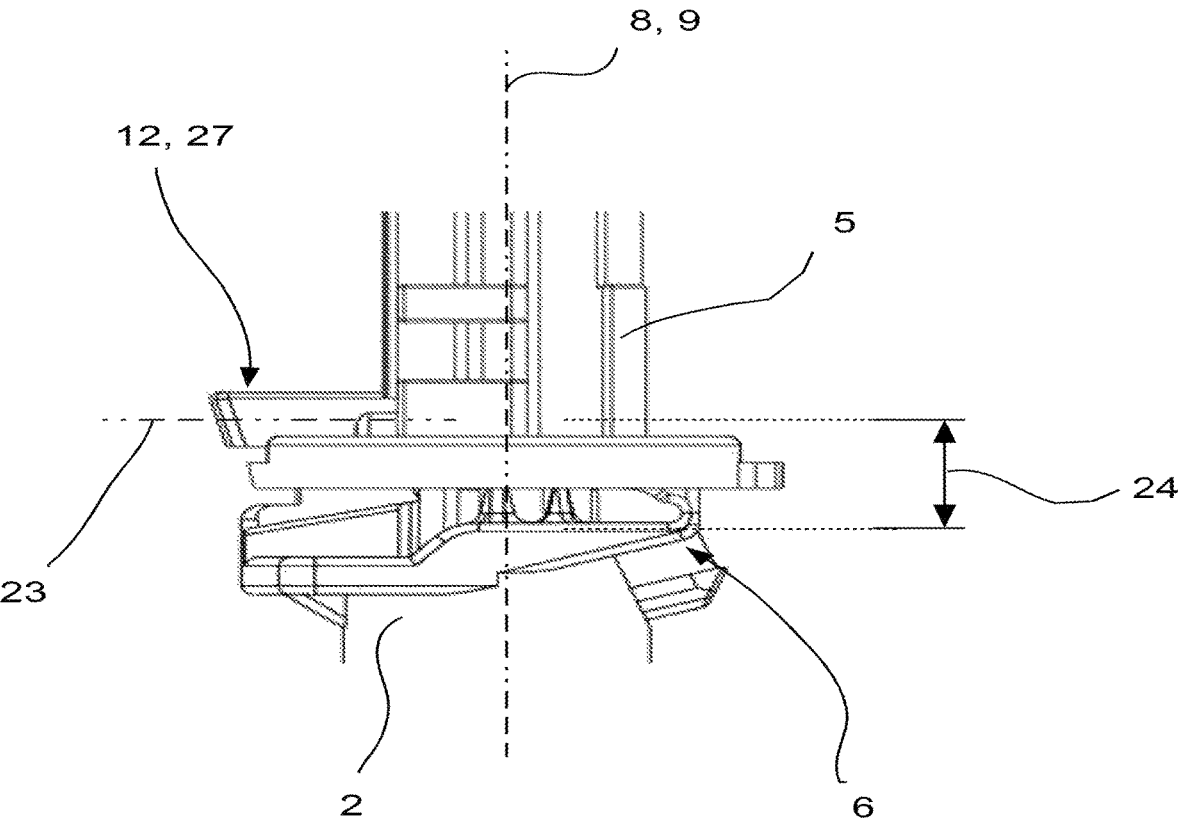
FIG. 3: A lateral view of the safety cover according to FIG. 1 in the region of the base.
Figure 4:
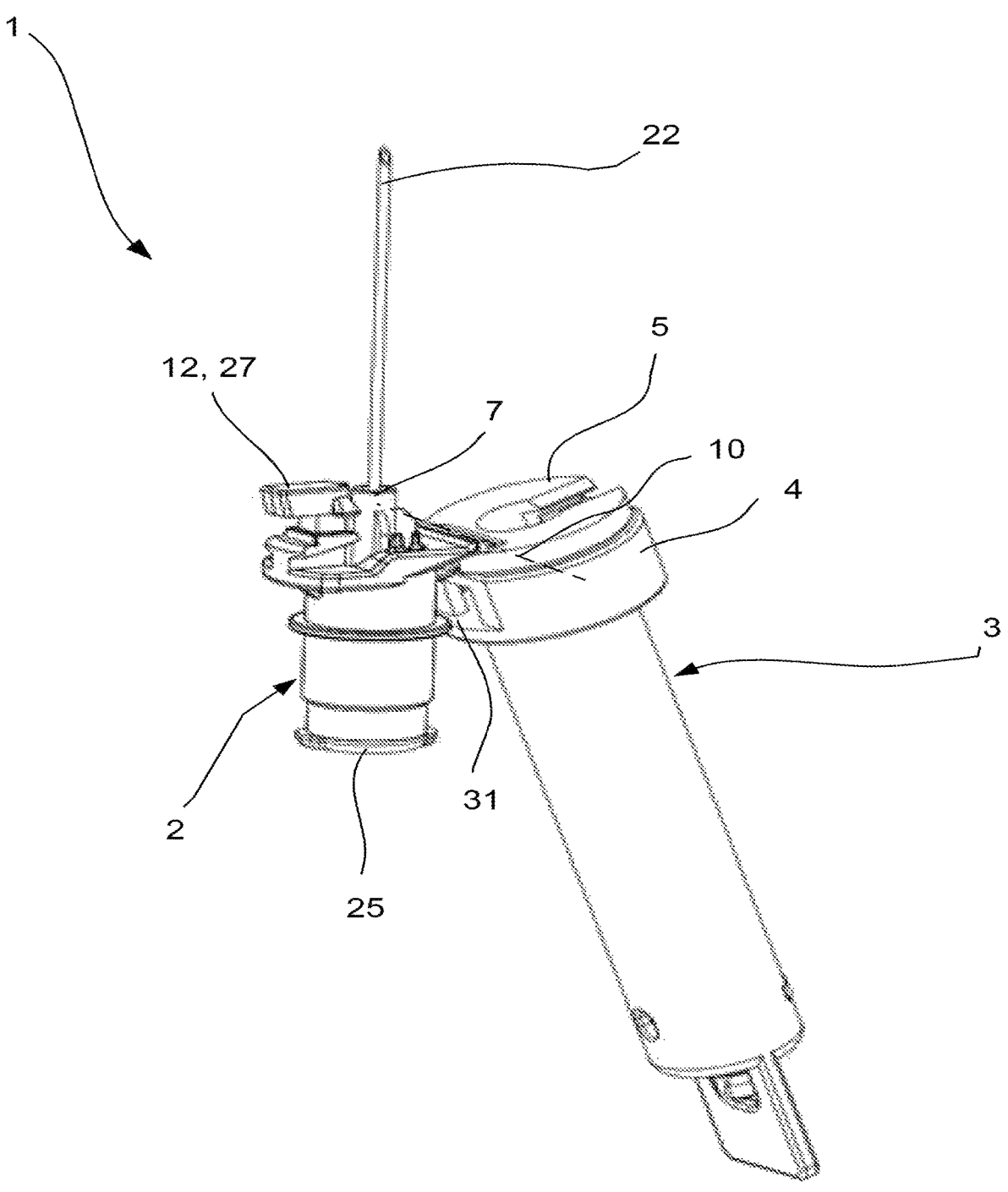
FIG. 4: The safety cover according to FIG. 1, wherein the cover is situated in its treatment position.
Figure 5:
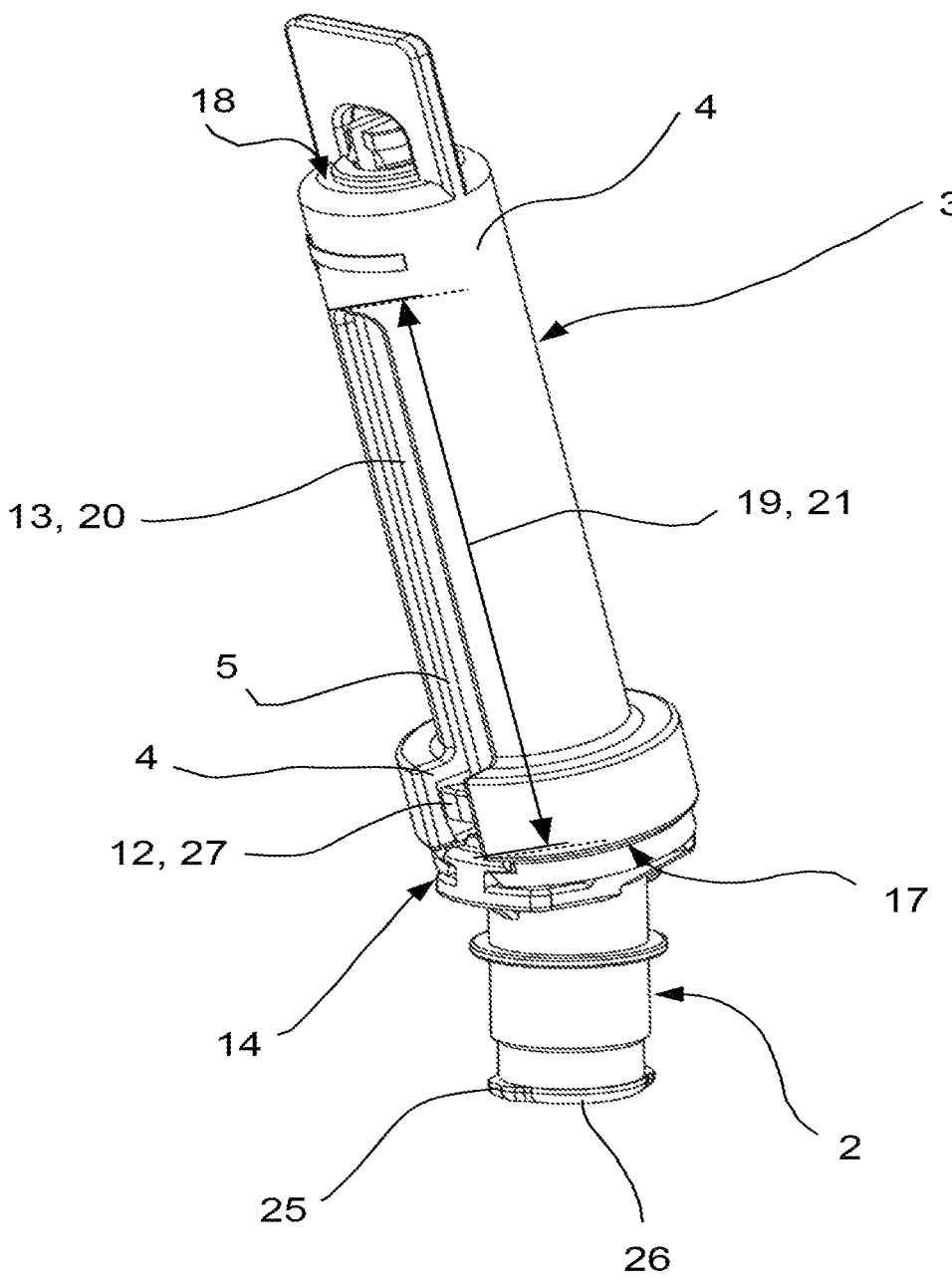
FIG. 5: The view according to FIG. 1, wherein the cover is situated in its end position.
Figure 6:
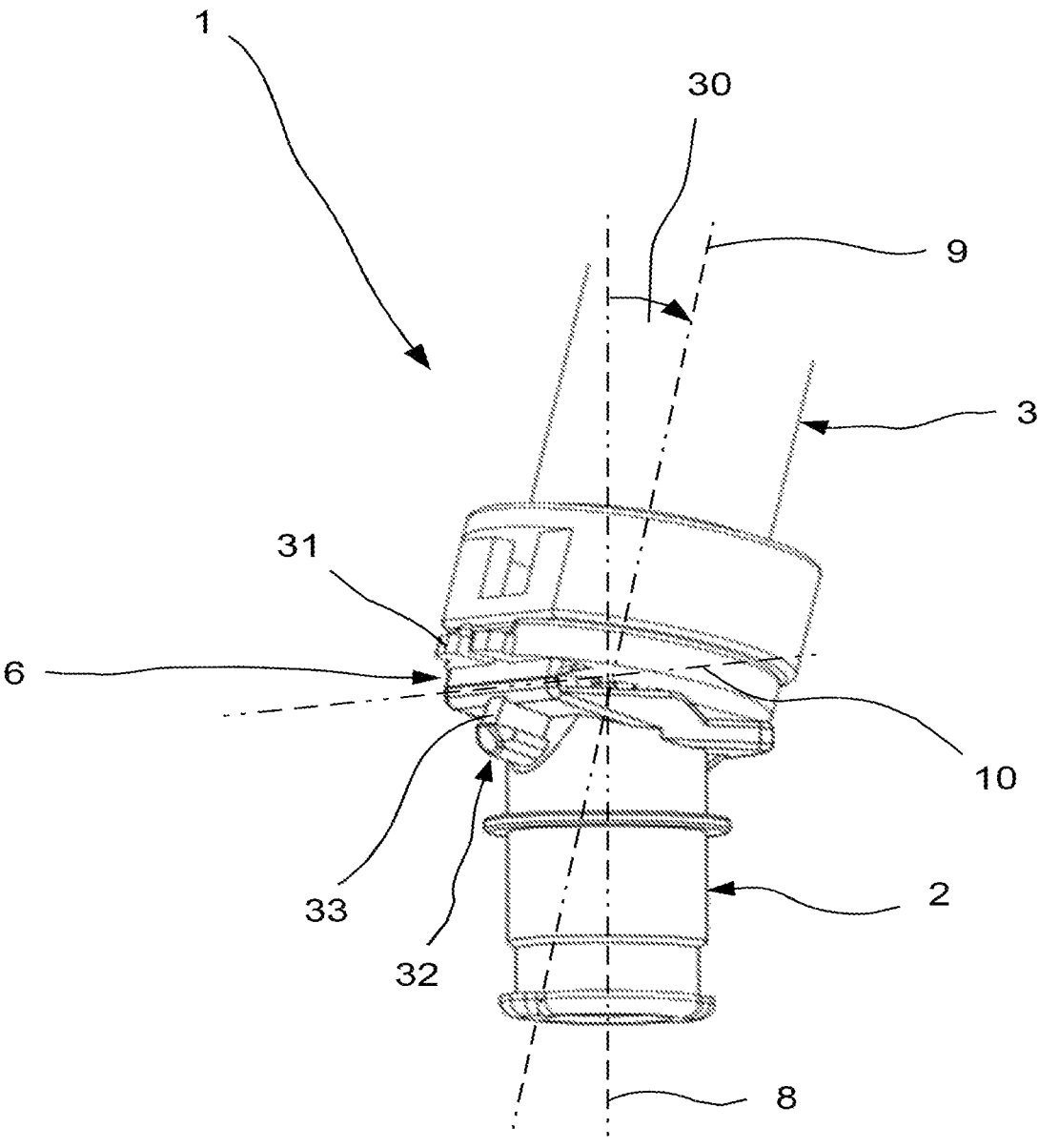
FIG. 6: The safety cover according to FIG. 5, however in the region of the base, viewed from the rear side.
Figure 7:
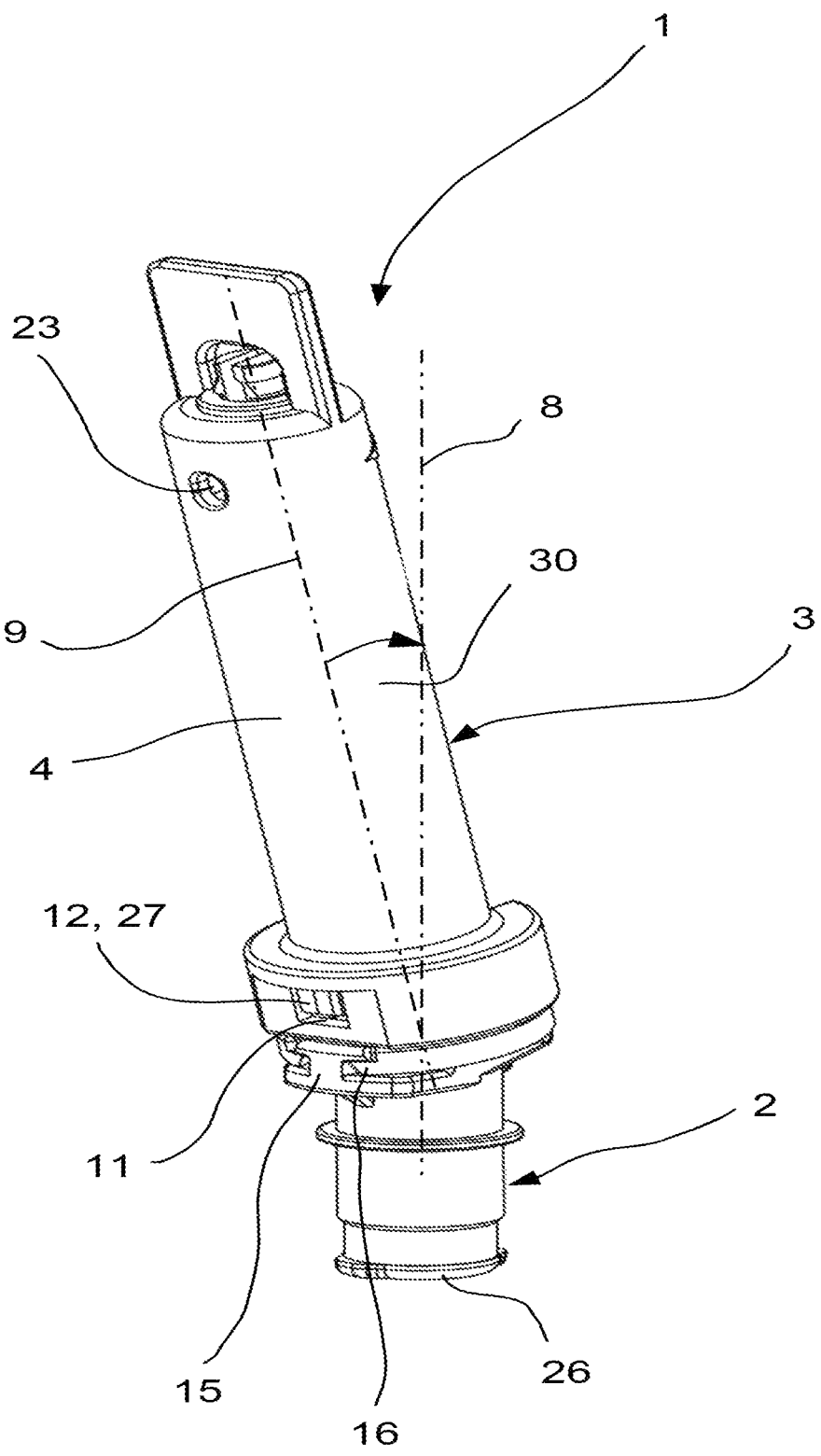
FIG. 7: The view according to FIG. 5, wherein an outer housing of the cover is situated in its locking position.
Figure 8:
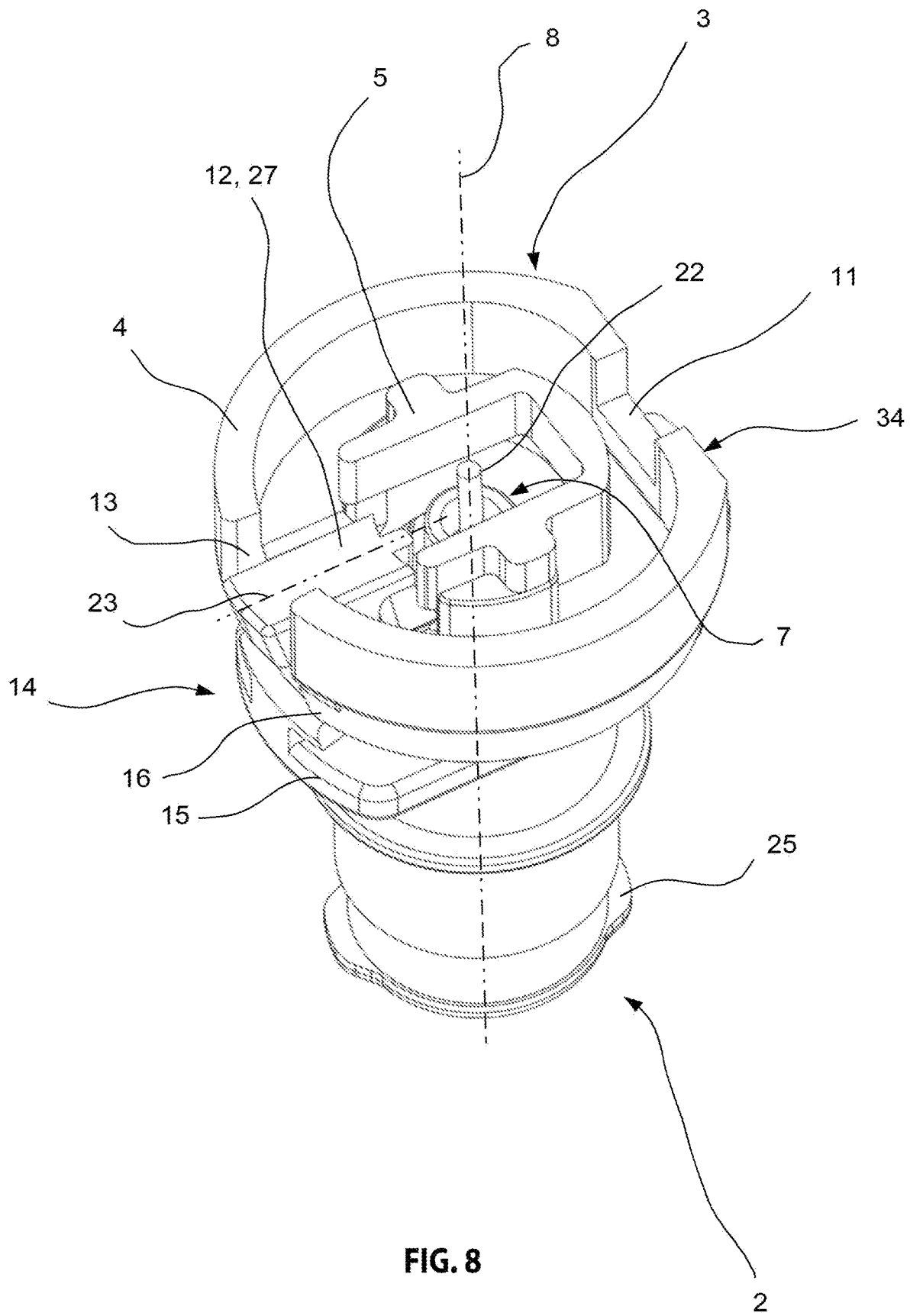
FIG. 8: A detail of the base of the safety cover according to FIG. 1, FIG. 9: A detail of the base of the safety cover according to FIG. 5, FIG. 10: A detail of the base of the safety cover according to FIG. 7.
Figure 9:
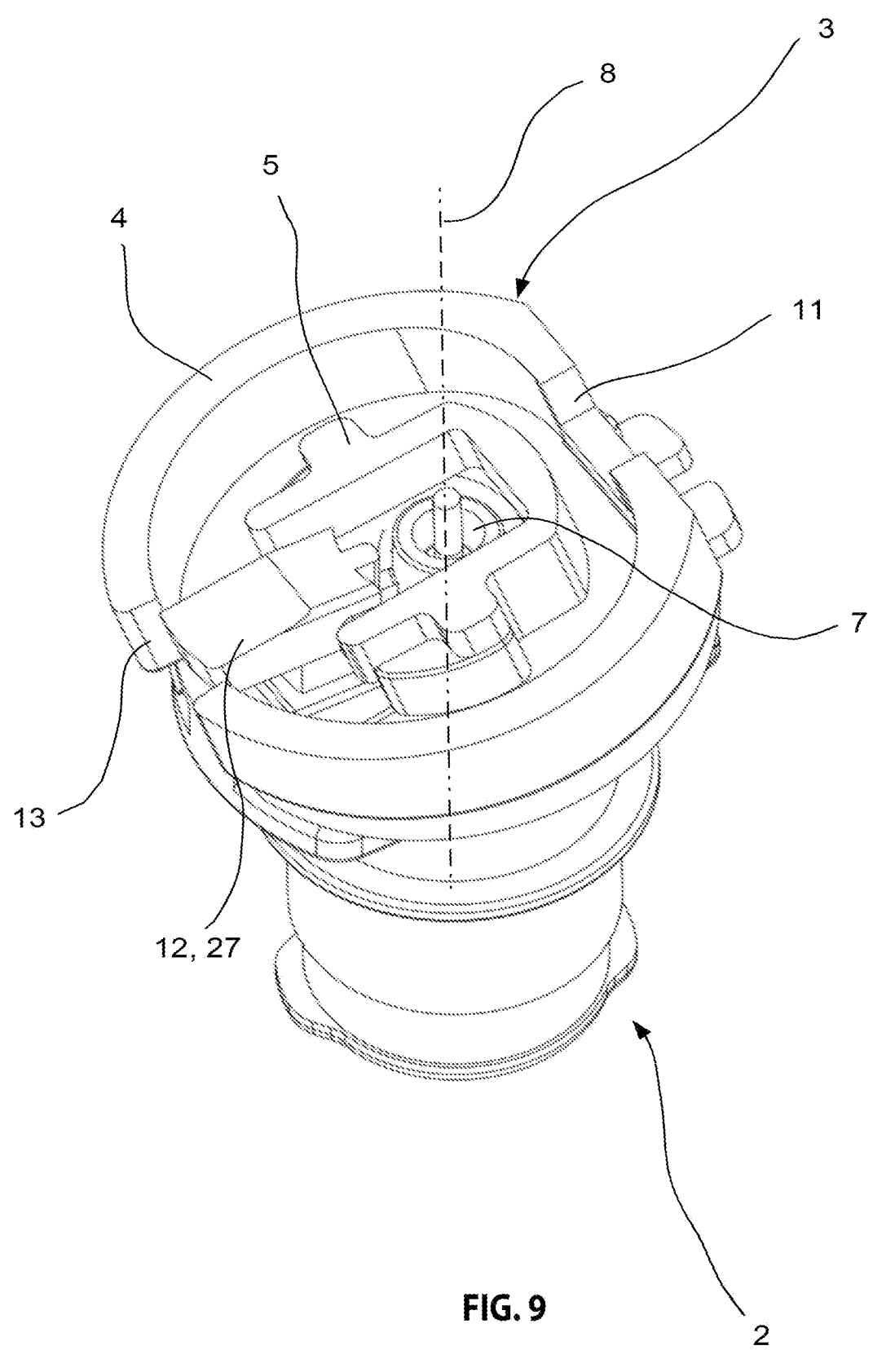
Figure 10:
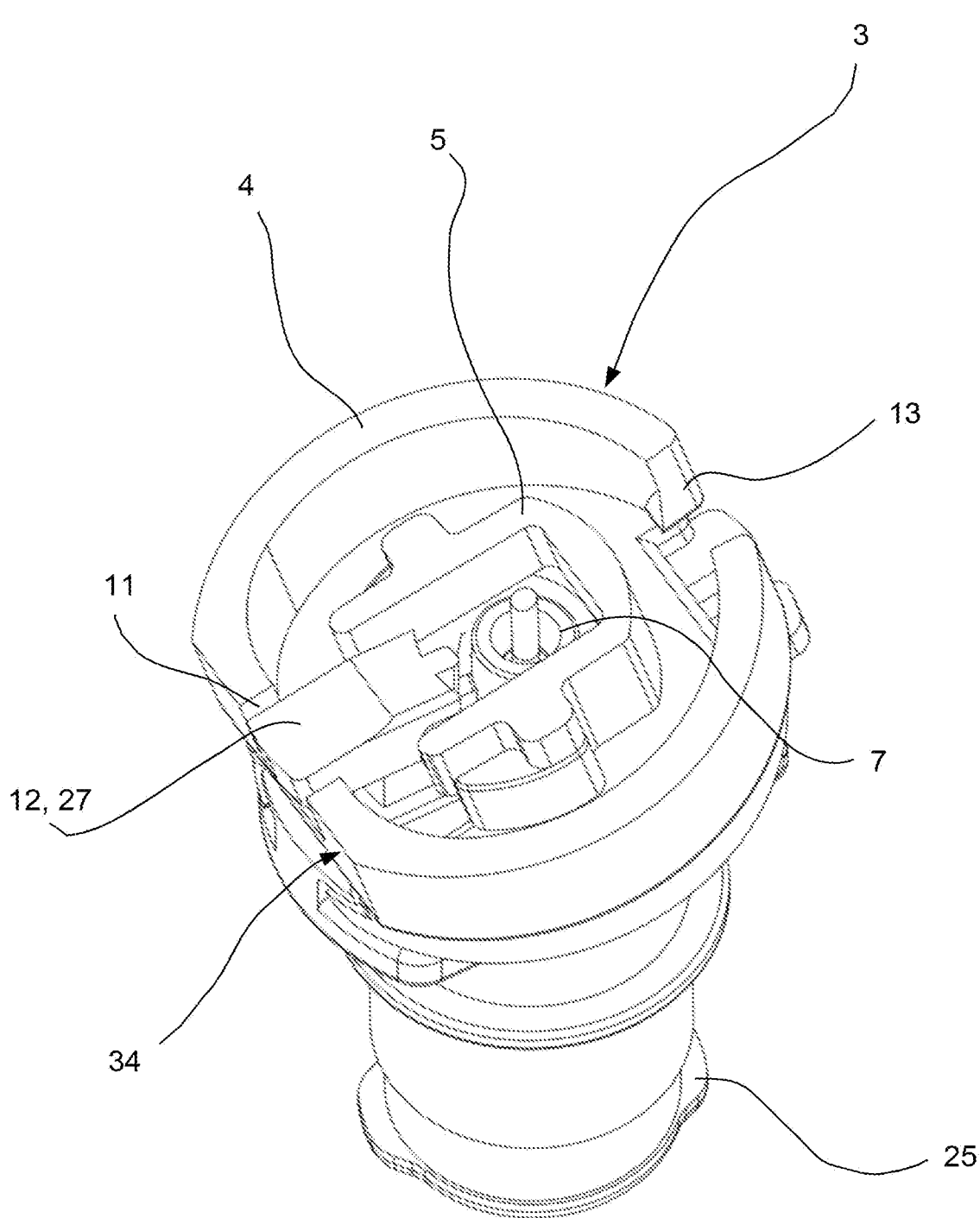

A safety cover 1 according to the invention, which is illustrated in FIGS. 1 to 10, comprises a base 2 and a cover 3, wherein the base 2 and the cover 3 are connected with one another by means of a hinge element 6 in a force-transferring manner. The cover 3 comprises an outer housing 4 and an inner housing 5. Both the outer housing 4 and also the inner housing 5 are coupled with one another in an elongated manner parallel to a longitudinal axis 9 of the cover 3 and coaxially. Furthermore, both the outer housing 4 and also the inner housing 5 are configured in a substantially rotationally symmetrical manner, wherein the coaxial arrangement basically enables an ability of the outer housing 4 to be twisted relative to the inner housing 5. This ability to be twisted is present here in relation to the longitudinal axis 9 of the cover 3. A force-transferring connection between the inner housing 5 and the outer housing 4 consists, in the example which is shown, by means of a detent nose 29, which penetrates an upper termination of the outer housing 4 at a distal end 18 of the cover 3 in axial direction of the cover 3. In this way, the outer housing 4 is mounted on the inner housing 5, wherein the outer housing 4 partially surrounds the inner housing 5.

In the example which is shown, the outer housing 4 and the inner housing 5 have recesses 13, 20 corresponding with one another, which are configured in an elongated manner. These recesses 13, 20 begin respectively starting from a proximal end 17 of the cover 3 and extend in a direction parallel to the longitudinal axis 9 of the cover 3 in the direction of the distal end 18 of the cover 3. Both recesses 13, 20 are equipped here with coinciding lengths 19, 21, which are measured parallel to the longitudinal axis 9 of the cover 3. These lengths 19, 21 amount here to ca. 3.5 cm.

The cover 3 lies firstly in its initial position, which can be seen with the aid of FIGS. 1 to 3 and 8. The base 2, which here likewise has a rotationally symmetrical shape, comprises in the example which is shown a locking device 12, which is configured in the form of an elongated pin 27. A longitudinal axis 23 of the locking device 12 extends in relation to a receiving axis 8 of a needle mount 7 of the base 2 in a radial direction and thereby projects radially over the remaining base 2. This can be seen particularly well with the aid of the detail illustration in FIG. 8. The locking device 12 extends in particular so far in radial direction that it surmounts radially the recess 13 of the outer housing 4 or respectively passes in radial direction through the recess 13. This embodiment has the result that the locking device 12 engages in a form-fitting manner with the outer housing 4, which thereupon abuts laterally against the locking device 12 in circumferential direction in relation to the longitudinal axis 9 of the cover 3. This engagement has the technical effect that the outer housing 4 is not able to be twisted freely relative to the base 2 and therefore relative to the inner housing 5 in relation to the longitudinal axis 9. This blocking of the ability of the outer housing 4 to be twisted in relation to the inner housing 5 is desired on presence of the cover 3 in its initial position, in order to prevent an unintentional transferring of the outer housing 4 into its locking position, in particular as a result of a screwing movement for re-tightening the safety cover 1 on an injection device. This is explained extensively above. The form-fitting connection of the locking device 12 with the outer housing 4 in the safety cover 1 according to the invention is present in particular on presence of the cover 3 in its initial position.

The hinge element 6 is formed here by a film hinge which forms a pivot axis 10. The hinge element 6 is connected on the one hand with the base 2 and on the other hand with an inner housing 5 of the cover 3. Here, the hinge element 6 is connected both to the base 2 and also to the inner housing 5 respectively on the edge side or respectively on its outer circumference. The hinge element 6 makes it possible that the cover 3 as a whole is pivotable about the pivot axis 10 relative to the base 2. The pivot axis 10 is oriented here perpendicularly to the receiving axis 8 of the needle mount 7. In this way, the cover 3 is pivotable, proceeding from the initial position shown in FIG. 1 into its treatment position shown in FIG. 4, on the presence of which the cover 3 is pivoted here through ca. 120° with respect to the initial position. The transferring of the cover 3 into the treatment position has the result that an injection needle 22, received by means of the needle mount 7 of the base 2, is freed. This injection needle 22, on presence of the cover 3 in its initial position, is enclosed spatially by the cover 3, so that no risk of injury originates from the injection needle 22 for a user of a respective injection device. In the case of the transferring of the cover 3 into the treatment position, the injection needle 22 exits out of the cover 3 through the recesses 13, 20 of the outer housing 4 and of the inner housing 5 which are overlapping one another, so that the injection needle 22 is finally freed.

Here, it is particularly advantageous if the cover 3 can be securely clamped on an anchor element 32 by means of a clamping element 31, which is arranged here at a proximal end of the inner housing 5, wherein the anchor element 32 is arranged on the base 2. For this, the clamping element 31 comprises two clamping jaws, arranged at a distance from one another, which are suitable to cooperate with an anchor portion 33 of the anchor element 32 in a clamping manner and to fix the cover 3 relative to the base 2 in this way. On presence of the cover 3 in the treatment position, which has now been adopted, the respective patient can be injected with the respective medicament in a particularly convenient manner, wherein the cover 3 presents no impediment for the user.

After completion of the injection, the cover 3 is transferred back into its initial position, proceeding from the treatment position. The injection needle 22 is therefore enclosed spatially again by the cover 3, so that no acute danger originates from it. However, it is readily possible to transfer the cover 3 back again into its treatment position and to free the injection needle 22 again. In order to prevent this, provision is made to transfer the outer housing 4 into a locking position, proceeding from its starting position, which the outer housing 4 has on presence of the cover 3 in its initial position and on the presence of which the recesses 13, 20 of the outer housing 4 and of the inner housing 5 overlap one another. On presence in this locking position, the outer housing 4 of the injection device 1 which is shown is twisted by 180° here about the longitudinal axis 9 of the cover 3 relative to the inner housing 5. This has the result that the recesses 13, 20 no longer overlap one another, so that an interior, spatially enclosed by the cover 3, is now completely enclosed. The transferring of the cover 3 back into its treatment position is thereupon no longer possible, because the injection needle 22 can no longer pass through recesses and thereby leave the cover 3.

As on the presence of the cover 3 in the initial position in the manner described above the locking device 12 engages in a form-fitting manner with the outer housing 4, the transferring of the outer housing 4 into the locking position is firstly not possible. For this, it is necessary beforehand to terminate the form fit between locking device 12 and outer housing 4. For this purpose, the safety cover 1 according to the invention offers the possibility of transferring the cover 3 into an end position, which can be seen here in particular with the aid of FIGS. 5 to 7 and 9 and 10. For transferring into the end position, the cover 3 is pivoted by means of the hinge element 6 in a pivoting direction about the pivot axis 10. This pivoting direction is opposed to the pivoting direction in which the cover 3 is pivoted on transferring from the initial position into the treatment position. The pivoting or respectively displacing of the cover 3 into the end position takes place here about an angle 30 of ca. 8°, wherein this angle 30 can be understood as being situated between the longitudinal axis 9 of the cover and the receiving axis 8 of the needle mount 7. In the example which is shown, the cover 3 is able to be detained in the end position, for which the safety cover 1 comprises a interlocking mechanism 14. The latter has interlocking partners 15, 16 corresponding to one another, wherein a first interlocking partner 16 is associated with the cover 3 and the second interlocking partner 16 is associated with the base 2. The interlocking partner 15 of the base 2 has two undercuts here, which can engage in a form-fitting manner with corresponding projections of the interlocking partner 16 of the cover 3.

The displacement of the cover 3 into the end position has the technical effect that the form fit between the locking device 12 and the outer housing 4 is terminated. This is achieved here in that the outer housing 4, as a result of the pivoting movement of the cover 3 about the pivot axis 10 undergoes a horizontal movement component oriented parallel to the longitudinal axis 23 of the locking device 12, which brings about a displacement of the outer housing 4 in axial direction of the locking device 12 beyond the locking device 12. The latter remains motionless meanwhile, because it is associated with the base 2. An axial length of the locking device 12 is coordinated to the displacement of the cover 3 in such a manner that the latter is sufficient in order to overcome the form-fitting engagement of the outer housing 4 with the locking device 12. This can be seen particularly well with the aid of FIG. 9. In the example which is shown, the locking device 12 extends in an advantageous manner in a direction radially with respect to the receiving axis 8, which lies opposite the hinge element 6. Accordingly, the locking device 12 and the hinge element 6 are arranged on the base 2 lying opposite one another in relation to the receiving axis 8. In addition, the locking device 12 and the hinge element 6 are arranged relative to one another in such a manner that between the locking device 12 and the pivot axis 10 a distance 24 is present, measured parallel to the receiving axis 8. This can be seen particularly well with the aid of FIG. 3. In this way, it is possible in a particularly simple manner to transmit the pivoting of the cover 3 in the direction of the end position into a movement component which can overcome the engagement between locking device 12 and outer housing 4.

After adopting the end position, the outer housing 4 is now able to be twisted freely with respect to the inner housing 5 and to the base 2, so that the outer housing 4 is finally able to be transferred in the desired manner, proceeding from its starting position, into its locking position. For this, the outer housing 4, as already explained, is twisted through 180° in relation to the longitudinal axis 9 of the cover 3. The injection needle 22 is thereupon securely enclosed within the cover 3. For bringing about the twisting, the safety cover 1 comprises here a grip tab 28, which adjoins the distal end 18 of the cover 3.

In order to ensure that the outer housing 4 can not be turned back again into its starting position, the outer housing 4 comprises a further recess 11, which is arranged on the outer housing 4 lying opposite the recesses 13. The recess 11 has an at least substantially square shape, wherein its cross-section is coordinated with a cross-section of the locking device 12. The recess 11 is arranged in addition in a radially set back portion 34 of the outer housing 4, so that a radially measured distance of the further recess 11 to the longitudinal axis 9 of the cover 3 is less than a radially measured distance between the elongated recess 13 and the longitudinal axis 9. This can be seen particularly well with the aid of FIG. 8. This embodiment has the effect that the recess 11, despite the presence of the cover 3 in its end position, can cooperate in a form-fitting manner with the locking device 12. This cooperation brings about a repeated form-fitting connection between the outer housing 4 and the locking device 12 and therefore prevents a further twisting of the outer housing 4 relative to the base 2 and the inner housing 5. In this way, the desired effect is achieved that the outer housing 4 has reached its locking position and can not readily leave this again. The injection needle 22 is therefore spatially enclosed permanently in a secure manner within the cover 3.

The safety cover 1 according to the invention is able to be used in the described manner particularly advantageously in connection with injection devices which have a screw connection. Such injection devices can be equipped in particular with a luer lock connection and can have an internal thread. So that the safety cover 1 can be screwed with such an injection device or respectively its associated internal thread, the base 2 in the example which is shown comprises at a lower end 26 a radially outwardly projecting collar 25. The latter is suitable to cooperate in a technically related manner to an external thread with the respective internal thread of an injection device, so that the safety cover 1 can be screwed onto such an injection device.

REFERENCE NUMERALS AND
DESIGNATIONS

1 safety cover
2 base
3 cover
4 outer housing
5 inner housing
6 hinge element
7 needle mount
8 receiving axis
9 longitudinal axis
10 pivot axis
11 recess
12 locking device
13 recess
14 interlocking mechanism
15 interlocking partner
16 interlocking partner
17 proximal end
18 distal end
19 length
20 recess
21 length
22 injection needle
23 longitudinal axis
24 distance
25 collar
26 end
27 pin
28 grip tab
29 detent nose
30 angle
31 clamping element
32 anchor element
33 anchor portion
34 portion

What is claimed is:

1. A safety cover for coupling with an injection device, the safety cover comprising:
a base;
a cover including an outer housing and an inner housing; and
a hinge,
wherein the base includes a needle mount which is configured for directed receiving of an injection needle along a receiving axis of the needle mount,
wherein the outer housing is coupled with the inner housing in a coaxial arrangement relative to a longitudinal axis of the cover and mounted at the inner housing, at least partially surrounding the inner housing,
wherein the cover is connected by the hinge with the base, so that the cover is pivotable relative to the base about a pivot axis formed by the hinge and oriented perpendicular to the receiving axis so that that the cover is pivotable from an initial position in a first pivoting direction into a treatment position,
wherein the longitudinal axis of the cover is aligned parallel to the receiving axis of the needle mount when the cover is in the initial position, so that the injection needle received in the needle mount is enclosed by the cover,
wherein the longitudinal axis of the cover is pivoted relative to the receiving axis of the needle mount when the cover is in the treatment position, so that the injection needle received in the needle mount is available for use,
wherein the outer housing is twistable relative to the inner housing at least in one rotation direction about the longitudinal axis of the cover,
wherein the outer housing includes at least one first recess and the base includes at least one locking device corresponding with the at least one first recess
wherein the at least one locking device projects radially outward relative to the receiving axis of the needle mount and is configured engage the at least one first recess by positive form locking and block a further twisting of the outer housing relative to the inner housing when the outer housing is in a locking position when the outer housing is twisted relative to the inner housing,
wherein the at least one locking device of the base engages the outer housing by positive form locking at least when the outer housing is in a starting position which is assumed by the outer housing at least when the cover in the initial position, so that a twisting of the outer housing relative to the inner housing is blocked by the at least one locking device,
wherein the cover is pivotable by the hinge about the pivot axis in a second pivoting direction that is opposite to the first pivoting direction, beyond the initial position of the cover into an end position of the cover, so that the outer housing is displaceable relative to the base and the cover is transferrable into the end position,
wherein an engagement of the at least one locking device with the outer housing is terminated and a twisting of the outer housing relative to the inner housing is enabled when the cover is in the end position.

2. The safety cover according to claim 1,
wherein the base includes the at least one locking device configured as a radially outward projecting pin which is configured to provide the positive form locking engagement of the at least one first recess of the outer housing when the outer housing is in the locking position and to provide the positive form locking engagement of the outer housing when the outer housing is the initial position.

3. The safety cover according to claim 2,
wherein the outer housing includes at least one second recess which is configured to provide the positive form locking engagement of the at least one locking device of the base,

wherein the at least one first recess and the at least one second recess of the outer housing are formed on the outer housing offset by 180° about the longitudinal axis of the cover, and wherein the at least one locking device engages the at least one second recess by positive form locking when the outer housing is in the initial position and the locking device engages the at least one first recess by positive form locking when the outer housing is in the locking position.

4. The safety cover according to claim 1, wherein the outer housing includes at least one second recess which is configured to provide the positive form locking engagement of the at least one locking device of the base, and wherein the at least one first recess and the at least one second recess of the outer housing are formed on the outer housing offset by 180° about the longitudinal axis of the cover.

5. The safety cover according to preceding claim 4, wherein the at least one second recess of the outer housing extends along the longitudinal axis of the cover from a proximal end towards a distal end of the cover, and wherein a length of the at least one second recess measured parallel to the longitudinal axis is at least 2.0 cm or at least 3.0 cm.

6. The safety cover according to claim 5, wherein the inner housing includes at least one third recess which extends along the longitudinal axis of the cover from a proximal end in the direction towards a distal end of the cover, wherein a length of the at least one third recess, measured parallel to the longitudinal axis of the cover, is at least 2.0 cm or at least 3.0 cm, and wherein the at least one second recess of the outer housing and the at least one third recess of the inner housing have shapes and lengths corresponding to one another.

7. The safety cover according to claim 5, wherein the inner housing includes at least one third recess which extends along the longitudinal axis of the cover from a proximal end in the direction towards a distal end of the cover, wherein a length of the at least one third recess, measured parallel to the longitudinal axis of the cover, is at least 2.0 cm or at least 3.0 cm, and wherein the at least one second recesses of the outer housing and the at least one third recess of the inner housing are aligned overlapping one another when the cover is in the initial position, so that the injection needle penetrates the at least one second recess and the at least one third recess when the cover is pivoted into the treatment position so that the injection needle is available for use.

8. The safety cover according to claim 5, wherein the at least one second recess of the outer housing and the at least one third recess of the inner housing are offset relative to one another when the outer housing is in the locking position, so that the cover is prevented from moving from the initial position into the treatment position.

9. The safety cover according to claim 1, further comprising:

an interlocking mechanism which includes a respective interlocking partner on the base and an interlocking partner on the cover, and wherein the interlocking partner on the base and the interlocking partner on the cover interlock with each other when the cover is in the end position, so that the cover is fixed in the end position.

10. The safety cover according to claim 1, wherein the inner housing includes at least one third recess which extends along the longitudinal axis of the cover from a proximal end in the direction towards a distal end of the cover, wherein a length of the at least one third recess, measured parallel to the longitudinal axis of the cover, is at least 2.0 cm or at least 3.0 cm.

11. The safety cover according to claim 1, wherein the base includes a radially projecting circumferential collar configured to cooperate with a thread of the injection device, so that the safety cover is threadable onto the injection device.

12. The safety cover according to claim 1, wherein the locking device and the hinge are arranged on the base opposite one another relative to the receiving axis.

13. The safety cover according claim 1, wherein the locking device and the hinge are arranged at a distance from one another, measured parallel to the receiving axis.

14. A safety cover for coupling with an injection device, the safety cover comprising:

a base;

a cover including an outer housing and an inner housing; and a hinge, wherein the base includes a needle mount which is configured for directed receiving of an injection needle along a receiving axis, wherein the outer housing is coupled with the inner housing relative to a longitudinal axis of the cover in a coaxial arrangement and mounted on the inner housing, at least partially surrounding the inner housing, wherein the inner housing is connected with the base by the hinge, so that the cover is pivotable relative to the base about a pivot axis formed by the hinge and oriented perpendicular to the receiving axis, so that the cover is pivotable from an initial position in a first pivoting direction into a treatment position, wherein the longitudinal axis is aligned parallel to the receiving axis when the cover in the initial position, so that an injection needle received in the needle mount is enclosable by the cover, wherein the longitudinal axis of the cover is pivoted relative to the receiving axis when the cover is in the treatment position, so that the injection needle received in the needle mount is available for use, wherein the outer housing is twistable relative to the inner housing at least in one rotation direction about the longitudinal axis of the cover, wherein the outer housing includes at least one first recess and the base includes at least one pin corresponding to the at least one first recess, wherein the pin projects radially outward relative to the receiving axis of the needle mount and is configured to engage the at least one first recess of the outer housing by positive form locking and block a further twisting of the outer housing relative to the inner housing when the outer housing is in a locking position twisted relative to the inner housing, wherein the outer housing includes at least one second recess, wherein the pin of the base engages the at least one second recess of the outer housing by positive form locking when the cover is in the initial position, so that the twisting of the outer housing relative to the inner housing is blocked, wherein the cover is pivotable in a second pivoting direction opposite to the first pivoting direction about the pivot axis beyond the initial position into an end position, and wherein the positive form locking of the pin in the second recess of the outer housing is terminated when the cover is in the end position, so that the twisting of the outer housing relative to the inner housing is enabled.

* * * * *